United States Patent
Maas et al.

(10) Patent No.: US 7,074,972 B2
(45) Date of Patent: Jul. 11, 2006

(54) SECONDARY $C_{10}$-$C_{18}$ SURFACTANT ALCOHOLS

(75) Inventors: Heiko Maas, Mannheim (DE); Juergen Tropsch, Roemerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 398 days.

(21) Appl. No.: 10/312,586

(22) PCT Filed: Jul. 16, 2001

(86) PCT No.: PCT/EP01/08197

§ 371 (c)(1), (2), (4) Date: Jan. 17, 2003

(87) PCT Pub. No.: WO02/08164

PCT Pub. Date: Jan. 31, 2002

(65) Prior Publication Data

US 2003/0176745 A1    Sep. 18, 2003

(30) Foreign Application Priority Data

Jul. 21, 2000 (DE) .................. 100 35 617

(51) Int. Cl.
*C07C 17/00* (2006.01)
(52) U.S. Cl. .................. 568/878; 568/14; 568/28
(58) Field of Classification Search ............... 570/700, 570/840, 876, 878; 568/878
See application file for complete search history.

(56) References Cited

U.S. PATENT DOCUMENTS

| | | | | |
|---|---|---|---|---|
| 2,088,015 A | * | 7/1937 | Wickert | 568/382 |
| 2,088,018 A | | 7/1937 | Freure et al. | |
| 4,101,586 A | * | 7/1978 | Deem et al. | 568/388 |
| 4,694,108 A | * | 9/1987 | Elliott | 568/387 |
| 6,765,119 B1 | * | 7/2004 | Hoffmann et al. | 568/881 |

FOREIGN PATENT DOCUMENTS

DE    0 850 907 A2  *  7/1998

OTHER PUBLICATIONS

E.E. Dreger et al.: "Sodium alcohol sulphates. Properties involving surface activity" Industrial and Engineering Chemistry, vol. 36, No. 7, pp. 610-617 Jul. 1944.

E. Keinan et al.: "Thermostable enzymes in organic synthesis. 7. Total synthesis of the western corn rootworm sex pheromone 8-methyldec-2-yl propanoate using a TBADH-generated C2-bifunctional chiron" Journal of Organic Chemistry, vol. 57, No. 13, pp. 3631-3636, Jun. 19, 1992.

A. Sharma et al.: "Studies on PPL-catalysed acetylation of 2-alkanols: its application for the synthetic of 2-dodecanol and 2-tridecyl acetate, the pheromones of crematogaster ants and *Drosophila mulleri* flies" Synthetic Communications, vol. 26, No. 1, pp. 19-25, 1996.

W. Schlenk, Jr.: "Das asymmetriche einschlussgitter des hamstoffs, III. Konfigurativ nicht-stetige gitterzuordnung der gastmolekuele" Liebigs Annalen Der Chemie, No. 7, pp. 1179-1194, Jul. 1973.

F.L. Breusch et al.: "Synthese der d,l-oxyparaffine mit 14 bls 23 kohlenstoffatomen (IV. Mitteil. Ueber isomere und homologe reihen)" Chemische Berichte, vol. 86, No. 5, pp. 678-684, May 1953.

D.F. Jones et al.: "Microbiological oxidation of long-chain aliphatic compounds. Part I. Alkanes and alk-1-enes" Journal of the Chemical Society, Section C, No. 22, pp. 2801-2808, 1968.

(Continued)

*Primary Examiner*—Porfirio Nazario-Gonzalez
(74) *Attorney, Agent, or Firm*—Oblon, Spivak, McClelland, Maier & Neustadt P.C.

(57) ABSTRACT

The invention relates to secondary $C_{10}$ to $C_{18}$ surfactant alcohols of the general formula (I), wherein R represents methyl or ethyl and R' represents a linear or branched alkyl group with 6–13 C atoms, excepting 5-ethyl-2-nonanol and 6-ethyl-3-decanol, in addition to fatty alcohol alkoxylates, alkyl phosphates, alkyl sulphates, alkyl ether phosphates and alkyl ether sulphates. The secondary $C_{10}$ to $C_{18}$ surfactant alcohols can be produced by a simple aldol condensation of linear or branched saturated or unsaturated $C_7$–$C_{14}$ aldehyde excepting 2-ethyl hexanal, with acetone or methyl ethyl ketone and the subsequent hydrogenation of the condensation product. In the preferred method, the aldol condensation is heterogenically catalyzed under hydrogenation conditions and the saturated ketone that has been formed is subsequently hydrogenated

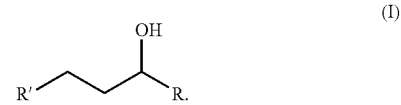

(I)

17 Claims, No Drawings

OTHER PUBLICATIONS

Y. Naoshima et al.: "Enzymatic preparation of entiomerically pure alkan-2- and -3-ols by liapse-catalysed hydrolysis with pseudomonas cepacia in the presence of organic media" Journal of the Chemical Society, Perkin Transactions 1, No. 5, pp. 557-561, Mar. 7, 1993.

T. Osawa: Enantioface-differentiating hydrogenation of 2-alkanones over modified Raney nickel Chemistry Letters, No. 11, pp. 1609-1612, Nov. 1985.

S. Schuering et al.: "Definierte oxaethylate von primaeren und sekundaeren alkoholen. Die synthese reiner polyaethylenglykolaether von n-Dodescanol, Tetradecanol-(2) und Tetradecanol-(6)" TENSIDE, vol. 4, No. 6, pp. 161-167, Jun. 1967.

F. Pueschel: "Synthese und grenzflaechenaktive eigenschaften der stellungsisomeren natrium- und kalium-n-hexadecylsulfate-(1) bis -(8) und einiger natrium- und kalium-1-(n-alkyl)-n-dodecylsulfate-(1)" TENSIDE, vol. 3, No. 3, pp. 71-80, Mar. 1966.

M. Ochiai et al.: "Triphenylphosphine-mediated olefination of aldehydes with (Z)-(2-acetoxyalk-1-enyl)phenyl-delta3-iodanes: generation and reaction of (2-oxoalkyl)phenyl-delta3-iodanes" Chemical Communications, No. 13, pp. 1157-1158, Jun. 16, 2000.

B.Z. Awen et al.: "An expedient synthesis of alpha,beta-unsaturated ketones using nitroalkanes and sulphones" Chemistry Letters, No. 5, pp. 767-768, May 1992.

M. Hinder et al.: "Die thermische zerstezung von alpha-keto-gamma-lactonen" Helvetica Chimica Acta, vol. 30, No. 6, pp. 1495-1501, Oct. 15, 1947.

R.D. Vukicevic et al.: "Use of a sacrificial aluminum anode in the acylation of some olefins" Bulletin of the Chemical Society of Japan, vol. 71, No. 4, pp. 899-904, Apr. 1998.

K. Hideg et al.: "Synthesis of various new nitroxide free radical fatty acids" Journal of the Chemical Society, Perkin Transactions 1, No. 8, pp. 1431-1438, Aug. 1986.

* cited by examiner

SECONDARY $C_{10}$-$C_{18}$ SURFACTANT ALCOHOLS

The invention relates to secondary $C_{10}$–$C_{18}$ surfactant alcohols, to processes for their preparation, to fatty alcohol alkoxylates, alkyl phosphates, alkyl ether phosphates, alkyl sulfates and alkyl ether sulfates prepared from the surfactant alcohols, and to the use thereof as surfactants.

Fatty alcohols with a chain length of from 8 to 18 carbon atoms are used for the preparation of nonionic and anionic surfactants. Nonionic surfactants are obtained by reacting the fatty alcohols with alkylene oxides to give the corresponding fatty alcohol ethoxylates. Here, the chain length and the degree of chain branching of the fatty alcohol influences various surfactant properties such as wetting ability, foam formation, fat-dissolving ability and cleaning power, and the biodegradability of the surfactants.

Anionic surfactants are obtained by converting the fatty alcohols to the corresponding alkyl phosphates or alkyl sulfates, or by converting the fatty alcohol alkoxylates to the alkyl ether phosphates or alkyl ether sulfates.

The preparation of said nonionic and anionic surfactants is described in Kosswig/Stache, Die Tenside [Surfactants], Carl Hanser Verlag, Munich, Vienna 1993, chapter 2.2 and 2.3.

Fatty alcohols which are suitable for the preparation of surfactants (surfactant alcohols) are obtainable from natural sources, for example from surfactant oils, or, however, are obtainable by a synthetic route. Examples are the "Ziegler alcohols", which are prepared on the basis of ethylene, or oxo alcohols prepared from long-chain linear olefins by hydroformylation.

The surfactant alcohols currently used are still predominantly primary alcohols. In addition to these, long-chain secondary alcohols are also gaining in importance. For example, EP-A 0 850 907 describes the addition of ethylene glycol onto long-chain α-olefins. The addition products, which can be regarded as monoethoxylated secondary alcohols, are obtainable as surfactant raw material under the trade name Softanole®. Secondary alcohols which are required, for example, for the preparation of alkyl sulfates and alkyl phosphates cannot be prepared by this process. Furthermore, the preparation starts from expensive α-olefins as raw material.

U.S. Pat. No. 2,088,018 describes the preparation of secondary alcohols by simple aldol condensation of aldehydes, namely 2-ethylhexaldehyde and butyraldehyde, onto ketones, namely methyl ethyl ketone, methyl amyl ketone, methyl isobutyl ketone, butylideneacetone, dipropyl ketone and methylheptanone, and the subsequent hydrogenation of the condensation products to give the saturated secondary alcohol. The aldol condensation of 2-ethylhexaldehyde onto methyl ethyl ketone and the hydrogenation of the condensation product to give 6-ethyl-3-decanol, and the subsequent sulfation thereof is described, inter alia. The use of the sulfate as surfactant is not mentioned.

Also described are certain pentadecyl sulfates and hexadecyl sulfates. Fatty alcohol alkoxylates, alkyl phosphates, alkyl ether phosphate and alkyl ether sulfates are not mentioned.

U.S. Pat. No. 2,088,015 describes the aldol condensation of 2-ethylhexaldehyde onto acetone, the hydrogenation of the condensation product to give 5-ethyl-2-nonanol and the sulfation thereof. The use of the sulfate as surfactant is not described.

Also known are 2,8-dimethyl-5-nonanol (CAS No. 19780-96-2), 3,9-dimethyl-6-undecanol (Beilstein Reg. No. 6122547) and 7-tridecanol (CAS No. 927-45-7). Their use as surfactant raw material is not mentioned in the corresponding abstracts.

It is an object of the present invention to provide further surfactant alcohols and also nonionic and anionic surfactants obtainable from these and having advantageous properties.

We have found that this object is achieved by secondary $C_{10}$ to $C_{18}$ surfactant alcohols of the formula (I)

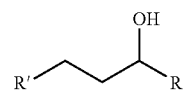

in which

R is methyl or ethyl and

R' is a linear or branched alkyl radical having 6–13 carbon atoms, with the exception of 5-ethyl-2-nonanol and 6-ethyl-3-decanol.

The surfactant alcohols of the formula (I) can be prepared by simple aldol condensations of linear or branched saturated or unsaturated $C_7$–$C_{14}$-aldehydes onto acetone or methyl ethyl ketone and subsequent hydrogenation of the condensation products. In this connection, preference is given to a process in which the aldol condensation is carried out with heterogeneous catalysis under hydrogenation conditions, and the saturated ketones formed are subsequently hydrogenated to give the secondary alcohols. Suitable hydrogenation catalysts for the reductive aldol condensation are described, for example, in DE-A 26 14 308. For example, 0.5% by weight of palladium oxide and 5% by weight of praseodymium oxide on aluminum oxide as heterogeneous catalyst can be used. The subsequent hydrogenation of the saturated ketone to give the secondary alcohol can be carried out in any manner familiar to the person skilled in the art, for example using Raney nickel as catalyst.

Suitable as $C_7$–$C_{14}$-aldehydes are, in principle, all isomeric linear and branched saturated and mono- or polyunsaturated $C_7$–$C_{14}$-aldehydes, preference being given to the saturated and monounsaturated aldehydes. Preference is thus given to all isomeric heptanals/heptenals, octanals/octenals, nonanals/nonenals, decanals/decenals, undecanals/undecenals, dodecanals/dodecenals, tridecanals/tridecenals and tetradecanals/tetradecenals.

Of these, particular preference is given to 2-ethylhexenal, which is obtainable, for example, by aldol condensation of n-butyraldehyde, and its hydrogenation product 2-ethylhexanal.

2-propylheptenal, which is obtainable, for example, by aldol condensation of n-valeraldehyde, and its hydrogenation product 2-propylheptanal;

technical-grade nonanal isomer mixtures obtainable by hydroformylation of technical-grade isooctene isomer mixtures, which can be obtained by dimerization of raffinate 2 ($C_4$ cut, consisting essentially of 1-butene, cis/trans-2-butene, butane and i-butane) over a nickel catalyst;

technical-grade undecanal isomer mixtures obtainable by hydroformylation of isodecene isomer mixtures, which can be obtained by dimerization of 1-pentene and/or 2-pentene, for example over a nickel catalyst.

technical-grade tridecanal isomer mixtures obtainable by hydroformylation of isododecene isomer mixtures, which can be obtained by dimerization of 1-hexene and/or 3-hexene, for example over a nickel catalyst;

mixtures of isomeric heptanals obtainable by hydroformylation of n-hexenes.

The surfactant alcohols of the formula (I) can be alkoxylated to give fatty alcohol alkoxylates. The secondary alcohols are preferably alkoxylated with $C_2$–$C_{17}$-α-olefin epoxides. It is possible to carry out the alkoxylation with one or more different α-olefin epoxides. The fatty alcohol alkoxylates prepared in this way preferably contain 1 to 200 alkylene oxide units. The surfactant alcohols can be alkoxylated with one or more different, preferably two different, alkylene oxides, it being possible to add different alkylene oxides onto the surfactant alcohol in randomly mixed manner or blockwise in targeted manner. Particularly preferred alkylene oxides are ethylene oxide, propylene oxide and 2-butylene oxide.

The present invention also provides the resulting fatty alcohol alkoxylates and their use as nonionic surfactants.

The secondary surfactant alcohols of the formula (I) and the fatty alcohol alkoxylates obtainable therefrom can also be phosphated by methods known to the person skilled in the art, for example by reaction with polyphosphoric acid, phosphoric acid or phosphorus pentoxide, to give the corresponding alkyl phosphates or alkyl ether phosphates respectively.

The present invention also provides the resulting alkyl phosphates and alkyl ether phosphates and their use as anionic surfactants.

The secondary surfactant alcohols of the formula (I) and the fatty alcohol alkoxylates obtainable therefrom can also be sulfated by methods known to the person skilled in the art, for example by reaction with sulfuric acid, sulfur trioxide or chlorosulfonic acid, to give the corresponding alkyl sulfates or alkyl ether sulfates respectively.

The present invention also provides the resulting alkyl sulfates, with the exception of 5-ethyl-2-nonyl sulfate and 6-ethyl-3-decyl sulfate, the resulting alkyl ether sulfates, and also the use of all of the resulting alkyl ether sulfates and alkyl sulfates as anionic surfactants.

The secondary surfactant alcohols of the formula (I) can also be used for the preparation of polyglucosides.

The preparation of the sulfates, phosphates, ether sulfates and ether phosphates from the alcohols is described, for example, in Kosswig/Stache, Die Tenside, Karl Hanser-Verlag, Vienna 1993, chapter 2.2 and 2.3.

The present invention also provides laundry detergents and cleaners comprising the fatty alcohol alkoxylates, alkyl phosphates, alkyl ether phosphates, alkyl sulfates and alkyl ether sulfates according to the invention as surfactants.

In laundry detergents, the surfactants according to the invention can be present with other nonionic and/or ionic surfactants. Further anionic surfactants are, for example, alkylbenzenesulfonates, α-olefinsulfonates, other alcohol sulfates and ether sulfates and sulfosuccinates. Further nonionic surfactants are, for example, alkyl aminoalkoxylates, other alkyl polyglucosides and amphoteric surfactants, such as alkylamine oxides and betaines.

The laundry detergents generally comprise customary additives such as builders and cobuilders, for example polyphosphates, zeolites, polycarboxylates, phosphonates, citrates and complexing agents, optical brighteners, colortransferring inhibitors, for example polyvinylpyrrolidone, extenders, for example sodium sulfate and magnesium sulfate, soil-release agents, for example polyethers, polyesters and carboxymethylcellulose, encrustation inhibitors, for example polyacrylates and acrylic acid/maleic acid copolymers, bleaches, for example perborate or percarbonate, bleach activators, for example tetraacetylethylenediamine, bleach stabilizers, perfume, foam-suppressing agents, for example silicone oils and alcohol propoxylates, enzymes, for example amylases, lipases, proteases or carboxylases, alkali donors, for example pentasodium metasilicate or sodium carbonate, and further additives familiar to the person skilled in the art. Additives are generally present in the laundry detergents in amounts of from 0.1 to 40% by weight, preferably 0.5 to 30% by weight, particularly preferably 1.0 to 20% by weight.

Liquid laundry detergents may additionally comprise solvents, for example ethanol, isopropanol, 1,2-propylene glycol or butylene glycol. Laundry detergents in the form of tablets generally comprise further additives, such as tableting auxiliaries, for example polyethylene glycols with molar masses of >1000 g/mol or polymer dispersions, tablet disintegrants, for example cellulose derivatives, crosslinked polyvinylpyrrolidone, crosslinked polyacrylates or combinations of acids such as citric acid with sodium carbonate.

Cleaners, such as machine dishwashing detergents, metal grease removers, glass cleaners and floor cleaners, can comprise, as customary additives, builders, for example polyphosphates, polycarboxylates, phosphonates and complexing agents, dispersants, for example naphthalenesulfonic acid condensates and polycarboxylates, pH regulators, for example NaOH, KOH, pentasodium metasilicate or acids, such as hydrochloric acid, phosphoric acid, amidosulfuric acid and citric acid, enzymes, for example lipases, amylases, proteases and carboxylases, perfume, dyes, biocides, for example isothiazolinones, 2-bromo-2-nitro-1,3-propanediol, bleaches, for example perborate or percarbonate, bleach activators, for example tetraacetylethylenediamine, bleach stabilizers, solubilizers, for example cumenesulfonates, toluenesulfonates, short-chain fatty acids and phosphoric alkyl or aryl esters and solvents, for example short-chain alkyloligoglycols, alcohols, such as ethanol or propanol, and aromatic solvents, such as toluene or xylene, N-alkylpyrrolidones and alkylene carbonates.

Cleaners in solid form can additionally comprise extenders.

Cleaners in tablet form may comprise, as further additives, said tableting auxiliaries and tablet disintegrants.

The fatty alcohol alkoxylates, alkyl phosphates, alkyl ether phosphates, alkyl sulfates and alkyl ether sulfates according to the invention can also be used as surfactants in a large number of other chemicotechnical processes.

The fatty alcohol alkoxylates, alkyl phosphates, alkyl ether phosphates, alkyl sulfates and alkyl ether sulfates according to the invention can be used in the metal-processing industry and may, for example, be present in cooling lubricants, hardening oils, hydraulic oil emulsions and polishing pastes, mold release agents, drawing oils, mordants, metal cleaners and metal dryers.

The fatty alcohol alkoxylates, alkyl phosphates, alkyl ether phosphates, alkyl sulfates and alkyl ether sulfates according to the invention can be used in the textile industry in the preparation and processing of textiles. For example, they may be present in pretreatment agents for fibers, dyeing auxiliaries, hand modifiers, hydrophobisization agents, auxiliaries for printing, antistats, flocculants and coatings, and can be used in the preparation of rayon fibers, spin finishes and textile melts.

The fatty alcohol alkoxylates, alkyl phosphates, alkyl ether phosphates, alkyl sulfates and alkyl ether sulfates according to the invention can be used as emulsifiers in the plastics-manufacturing and plastics-processing industry, for example in the preparation of plastics dispersions, bead polymers, foams, microcapsules for improving the adhesion between fillers and synthetic materials, as an additive to plastics dispersions for achieving particular effects such as foamability, filler compatibility or wetting ability, for coloring plastics, for the antistatic finishing of plastics, as emulsifiers for nonaqueous systems, and in interface-active mold release agents and adhesives.

The fatty alcohol alkoxylates, alkyl phosphates, alkyl ether phosphates, alkyl sulfates and alkyl ether sulfates according to the invention can also be used in the leather, paper, printing, electroplating and photographic industry. They may be present, for example, in surface coatings, pigments and printing inks or may be used in nonaqueous systems as dispersion auxiliaries, antisettling agents or leveling auxiliaries. In aqueous systems, they can be used for stabilizing plastics dispersions used as binders, as dispersion auxiliaries for organic and inorganic pigments, and for improving the adhesion properties of paints.

The fatty alcohol alkoxylates, alkyl phosphates, alkyl ether phosphates, alkyl sulfates and alkyl ether sulfates according to the invention can also be used in waste water purification or may be present in crop protection formulations.

The invention is illustrated in more detail by the examples below.

EXAMPLE 1

430 g of a nonanal isomer mixture (from the Rh-catalyzed hydroformylation of isooctene, prepared in accordance with WO 99/36382) and 870 g of acetone are introduced into a 2.5 l autoclave, and 86 g of a catalyst consisting of 0.5% by weight of PdO and 5% by weight of praseodymium oxide on $Al_2O_3$ are added. Hydrogen is injected to a pressure of 2 bar and the autoclave is heated to 160° C. During the reaction time of 24 h, a pressure of 40 bar is kept constant by the injection of fresh hydrogen. The reaction mixture is cooled and, after separating off the catalyst by filtration, is analyzed using gas chromatography. The conversion of the nonanals is 97%. The selectivity to dodecanols and dodecanones is 98%.

EXAMPLE 2

Isopropanol and acetone are removed by distillation from 2550 g of a product mixture obtained as in Example 1. 50 g of Raney nickel are then added. Hydrogenation is then carried out in a 2.5 l autoclave at a hydrogen pressure of 280 bar and a reaction temperature of 150° C. During the reaction time of 24 h, the pressure is kept constant by injection of fresh hydrogen. The reaction mixture is cooled and the catalyst is filtered off. The product mixture is distilled. At 95–103° C./4 mbar, 913 g of 2-dodecanol isomers are isolated. The product has a degree of branching of 1.4.

EXAMPLE 3

594 g of a tridecanal isomer mixture (from the Rh-catalyzed hydroformylation of isododecene) and 696 g of acetone are introduced into a 2.5 l autoclave, and 86 g of a catalyst consisting of 0.5% by weight of PdO and 5% by weight of praseodymium oxide on $Al_2O_3$ are added. Hydrogen is injected to a pressure of 2 bar and the autoclave is heated to 160° C. During the reaction time of 24 h, a pressure of 40 bar is kept constant by injection of fresh hydrogen. The reaction mixture is cooled and, after removal of the catalyst by filtration, is analyzed using gas chromatography. The conversion of the tridecanals is 98%. The selectivity to hexadecanones is 93%.

EXAMPLE 4

Isopropanol and acetone are separated off by distillation from 2490 g of a product mixture obtained as in Example 3. 50 g of Raney nickel are then added.

Hydrogenation is carried out in a 2.5 l autoclave at a hydrogen pressure of 280 bar and a reaction temperature of 150° C. During the reaction time of 24 h, the pressure is kept constant by injection of fresh hydrogen. The reaction mixture is cooled and the catalyst is filtered off. The product mixture is distilled. At 128–134° C./1 mbar, 1141 g of 2-hexadecanol isomers are isolated. The product has a degree of branching of 1.8.

EXAMPLE 5

463 g of an isomer mixture of 2-propylheptenal and 4-methyl-2-propylhexenal and 696 g of acetone are introduced into a 2.5 l autoclave, and 86 g of a catalyst consisting of 0.5% by weight of PdO and 5% by weight of praseodymium oxide on $Al_2O_3$ are added. Hydrogen is injected to a pressure of 2 bar and the autoclave is heated to 160° C. During the reaction time of 24 h, a pressure of 40 bar is kept constant by injection of fresh hydrogen. The reaction mixture is cooled and, after removal of the catalyst by filtration, is analyzed using gas chromatography. The conversion of the decenals is 93%. The selectivity to tridecanones is 84%.

EXAMPLE 6

Isopropanol and acetone are separated off by distillation from 2470 g of a product mixture obtained as in Example 5. 50 g of Raney nickel are then added. Hydrogenation is carried out in a 2.5 l autoclave at a hydrogen pressure of 280 bar and a reaction temperature of 150° C. During the reaction time of 24 h, the pressure is kept constant by injection of fresh hydrogen. The reaction mixture is cooled and the catalyst is filtered off. The product mixture is distilled. At 107–111° C./1 mbar, 874 g of 2-tridecanol isomers were isolated. The product has a degree of branching of 1.0.

EXAMPLE 7

Preparation of an Alcohol Ethoxylate with 7 mol of Ethylene Oxide 372 g of 2-dodecanol isomer mixture (prepared as in Example 2) are introduced with 1.5 g of NaOH into a dry 2 l autoclave. The autoclave contents are heated to 120° C., and 616 g of ethylene oxide are injected into the autoclave under pressure. After the total amount of ethylene oxide is present in the autoclave, the autoclave is kept at 120° C. for 60 minutes. After cooling, the catalyst is neutralized with acetic acid.

The resulting surfactant has a cloud point of 73° C., measured at 1% strength by weight in 10% strength by weight diethylene glycol butyl ether solution in accordance with DIN 53917. The surface tension at a concentration of 1 g/l is 26.4 mN/m, measured in accordance with DIN 53914.

EXAMPLE 8

Preparation of an Alcohol Ethoxylate with 3 mol of Ethylene Oxide 558 g of 2-dodecanol isomer mixture (prepared as in Example 2) are introduced with 1.5 g of NaOH into a dry 2 l autoclave. The autoclave contents are heated to 140° C., and 396 g of ethylene oxide are injected into the autoclave under pressure. After the total amount of ethylene oxide is present in the autoclave, the autoclave is kept at 140° C. for 45 minutes. After cooling, the catalyst is neutralized with sulfuric acid.

The resulting surfactant has a cloud point of 39° C., measured at 1% strength by weight in 10% strength by weight diethylene glycol butyl ether solution in accordance with DIN 53917. The surface tension at a concentration of 1 g/l is 26.5 mN/m, measured in accordance with DIN 53914.

EXAMPLE 9

Preparation of an Alcohol Ethoxylate with 14 mol of Ethylene Oxide 363 g of 2-hexadecanol isomer mixture (prepared as in Example 4) are introduced with 1.0 g of NaOH into a dry 2 l autoclave. The autoclave contents are heated to 120° C., and 924 g of ethylene oxide are injected into the autoclave under pressure. After the total amount of ethylene oxide is present in the autoclave, the autoclave is kept at 120° C. for 60 minutes. After cooling, the catalyst is neutralized with acetic acid.

The resulting surfactant has a cloud point of 88.5° C., measured at 1% strength by weight in water in accordance with DIN 53917. The surface tension at a concentration of 1 g/l is 27.7 mN/m, measured in accordance with DIN 53914.

EXAMPLE 10

Preparation of an Alcohol Ethoxylate with 5 mol of Ethylene Oxide 558 g of 2-hexadecanol isomer mixture (prepared as in Example 4) are introduced with 1.5 g of NaOH into a dry 2 l autoclave. The autoclave contents are heated to 130° C., and 396 g of ethylene oxide are injected into the autoclave under pressure. After the total amount of ethylene oxide is present in the autoclave, the autoclave is kept at 130° C. for 50 minutes. After cooling, the catalyst is neutralized with sulfuric acid.

The resulting surfactant has a cloud point of 60° C., measured at 1% strength by weight in 10% strength by weight diethylene glycol butyl ether solution in accordance with DIN 53917. The surface tension at a concentration of 1 g/l is 27.4 mN/m, measured in accordance with DIN 53914.

EXAMPLE 11

Preparation of an Alcohol Ethoxylate with 6 mol of Ethylene Oxide 400 g of tridecanol isomer mixture (prepared as in Example 6) are introduced with 1.5 g of NaOH into a dry 2 l autoclave. The autoclave contents are heated to 120° C., and 528 g of ethylene oxide are injected into the autoclave under pressure. After the total amount of ethylene oxide is present in the autoclave, the autoclave is kept at 120° C. for 60 minutes. After cooling, the catalyst is neutralized with acetic acid.

The resulting surfactant has a cloud point of 70° C., measured at 1% strength by weight in 10% strength by weight diethylene glycol butyl ether solution in accordance with DIN 53917. The surface tension at a concentration of 1 g/l is 27.0 mN/m, measured in accordance with DIN 53914.

EXAMPLE 12

Preparation of an Alcohol Ethoxylate with 3 mol of Ethylene Oxide 600 g of 2-tridecanol isomer mixture (prepared as in Example 6) are introduced with 1.5 g of NaOH into a dry 2 l autoclave. The autoclave contents are heated to 140° C., and 396 g of ethylene oxide are injected into the autoclave under pressure. After the total amount of ethylene oxide is present in the autoclave, the autoclave is kept at 140° C. for 45 minutes. After cooling, the catalyst is neutralized with sulfuric acid.

The resulting surfactant has a cloud point of 40.5° C., measured at 1% strength by weight in 10% strength by weight diethylene glycol butyl ether solution in accordance with DIN 53917. The surface tension at a concentration of 1 g/l is 27.0 mN/m, measured in accordance with DIN 53914.

We claim:

1. A process for the preparation of surfactant alcohols, comprising aldol condensation of at least one linear or branched saturated or unsaturated $C_7$–$C_{14}$-aldehydes onto acetone or methyl ethyl ketone, wherein the aldehyde is chosen from
   - 2-ethylhexenal
   - 2-propylheptenal
   - technical-grade mixtures of isomeric nonanals;
   - technical-grade mixtures of isomeric undecanals;
   - technical-grade mixtures of isomeric tridecanals;
   - mixtures of isomeric heptanals, and
   - mixtures thereof, and wherein the aldol condensation is carried out with heterogeneous catalysis under hydrogenating conditions.

2. A process as claimed in claim 1, wherein saturated ketone formed is subsequently hydrogenated.

3. A process as claimed in claim 2, further comprising the step of addition of alkylene oxides onto the obtained surfactant alcohols.

4. A process as claimed in claim 3, wherein one or more different $C_2$–$C_{17}$-α-olefin epoxides are added.

5. A process as claimed in claim 4, wherein the α-olefin epoxide is chosen from the group consisting of ethylene oxide, propylene oxide and 2-butylene oxide.

6. A process as claimed in claim 4, wherein at least two different alkylene oxides are added in blocks or randomly mixed.

7. A process as claimed in claim 1, further comprising the step of phosphation of the obtained surfactant alcohols.

8. A process as claimed in claim 3, further comprising the step of phosphation of the obtained surfactant alcohol alkoxylates.

9. A process as claimed in claim 1, further comprising the step of sulfation of the obtained surfactant alcohols.

10. A process as claimed in claim 3, further comprising the step of sulfation of the obtained surfactant alcohols alkoxylates.

11. A process as claimed in claim 1, wherein
said technical-grade mixtures of isomeric nonanals are obtained by hydroformylation of isooctene isomer mixtures from the dimerization of raffinate 2;
said technical-grade mixtures of isomeric undecanals are obtained by hydroformylation of isodecene isomer mixtures from the dimerization of 1-pentene and/or 2-pentene;
said technical-grade mixtures of isomeric tridecanals are obtained by hydroformylation of isododecene isomer mixtures from the dimerization of 1-hexene and/or 3-hexene; and
said mixtures of isomeric heptanals are obtained by hydroformylation of n-hexenes.

12. A process as claimed in claim 1, wherein the at least one aldehyde comprises 2-ethylhexenal.

13. A process as claimed in claim 1, wherein the at least one aldehyde comprises 2-propylheptenal.

14. A process as claimed in claim 1, wherein the at least one aldehyde comprises a technical-grade mixture of isomeric nonanals.

15. A process as claimed in claim 1, wherein the at least one aldehyde comprises a technical-grade mixture of isomeric undecanals.

16. A process as claimed in claim 1, wherein the at least one aldehyde comprises a technical-grade mixture of isomeric tridecanals.

17. A process as claimed in claim 1, wherein the at least one aldehyde comprises a mixture of isomeric heptanals.

* * * * *